United States Patent
Donnelly et al.

(10) Patent No.: US 11,951,189 B2
(45) Date of Patent: Apr. 9, 2024

(54) TARGETING COMPOUNDS AND METHODS FOR THEIR PRODUCTION

(71) Applicant: THE UNIVERSITY OF MELBOURNE, The University Of Melbourne (AU)

(72) Inventors: Paul Stephen Donnelly, Melbourne (AU); Nicholas Alan Zia, Melbourne (AU)

(73) Assignee: Clarity Pharmaceuticals Ltd, Eveleigh (AU)

( * ) Notice: Subject to any disclaimer, the term of this patent is extended or adjusted under 35 U.S.C. 154(b) by 0 days.

(21) Appl. No.: 17/046,053

(22) PCT Filed: Apr. 11, 2019

(86) PCT No.: PCT/AU2019/050322
§ 371 (c)(1),
(2) Date: Oct. 8, 2020

(87) PCT Pub. No.: WO2019/195888
PCT Pub. Date: Oct. 17, 2019

(65) Prior Publication Data
US 2021/0030900 A1 Feb. 4, 2021

(30) Foreign Application Priority Data
Apr. 11, 2018 (AU) .............................. 2018901197

(51) Int. Cl.
*A61B 5/00* (2006.01)
*A61B 8/00* (2006.01)
*A61B 10/00* (2006.01)
*A61K 51/04* (2006.01)
*C07D 487/08* (2006.01)

(52) U.S. Cl.
CPC ........ *A61K 51/0482* (2013.01); *A61K 51/044* (2013.01); *C07D 487/08* (2013.01)

(58) Field of Classification Search
CPC .............. A61K 51/0482; A61K 51/044; A61K 31/395; A61K 45/06; A61K 51/0495; A61K 33/34; A61K 51/1045; A61K 51/1063; C07D 487/08; C07D 403/12; C07D 403/14; A61P 35/00
See application file for complete search history.

(56) References Cited

U.S. PATENT DOCUMENTS 9,701,694 B2 * 7/2017 Donnelly ........... A61K 51/0482
2016/0331852 A1 * 11/2016 Zeglis ................ A61K 47/6897

FOREIGN PATENT DOCUMENTS

| WO | 2010/063069 A1 | 6/2010 |
| WO | WO-2012156918 A1 * | 11/2012 ........... A61K 31/435 |
| WO | 2013/082656 A1 | 6/2013 |
| WO | 2016/182804 A1 | 11/2016 |

OTHER PUBLICATIONS

Meyer et al. (J. Med. Chem. 2017, 60,8201-8217).*
Alt et al., A versatile approach for the site-specific modification of recombinant antibodies using a combination of enzyme-mediated bioconjugation and click chemistry. Angew Chem Int Ed Engl. Jun. 22, 2015;54(26):7515-9.
Cook et al., Pretargeted PET Imaging Using a Site-Specifically Labeled Immunoconjugate. Bioconjug Chem. Aug. 17, 2016;27(8):1789-95.
Gourmi et al., Labeled Macrobicyclic Sarcophagine Coupled to a GRP Receptor Antagonist Shows Great Promise for PET Imaging of Prostate Cancer. Mol Pharm. Aug. 3, 2015;12(8):2781-90.
Paterson et al., Enzyme-mediated site-specific bioconjugation of metal complexes to proteins: sortase-mediated coupling of copper-64 to a single-chain antibody. Angew Chem Int Ed Engl. Jun. 10, 2014;53(24):6115-9.
Paterson et al., PET imaging of tumours with a 64Cu labeled macrobicyclic cage amine ligand tethered to Tyr3-octreotate. Dalton Transactions. 2013;43(3):1386-1396.
Zeglis et al., Optimization of a Pretargeted Strategy for the PET Imaging of Colorectal Carcinoma via the Modulation of Radioligand Pharmacokinetics. Mol Pharm. Oct. 5, 2015;12(10):3575-87.
International Search Report and Written Opinion for Application No. PCT/AU2019/050322, dated May 16, 2019, 12 pages.

* cited by examiner

*Primary Examiner* — Michael G. Hartley
*Assistant Examiner* — Melissa J Perreira
(74) *Attorney, Agent, or Firm* — McCarter & English, LLP; Maria Laccotripe Zacharakis

(57) ABSTRACT

The present invention is directed to sarcophagine based compounds of formula (I). The compounds can complex a radioisotope, such as 64-copper and hence are useful in radioimaging and radiotherapy of cancers, e.g. colorectal cancer. The compounds work via a pre-targeting imaging approach in which the tetrazine reacts via click chemistry with a functional group such as a transcyclooctene which is pre-bound to a ligand such as a tumour specific antibody.

Formula (I)

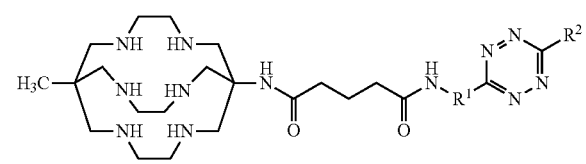

16 Claims, No Drawings

TARGETING COMPOUNDS AND METHODS FOR THEIR PRODUCTION

RELATED APPLICATIONS

This application is a 35 U.S.C. § 371 National Stage filing of International Application No. PCT/AU2019/050322, filed on Apr. 11, 2019, which in turn claims the benefit of Australian Patent Application No. 2018901197, filed on Apr. 11, 2018. The entire contents of each of the foregoing applications are incorporated herein by reference.

FIELD

The present invention relates to targeting compounds and methods for their production.

BACKGROUND

Ligands containing a radioisotope are often used in radiotherapy and diagnostic imaging. The ligand functions by directly targeting a particular site, for example, a particular receptor on a cell. Where the ligand is intended for the treatment or imaging of a cancer or similar proliferative disorder, the site to be targeted may be a receptor that is expressed on the surface of the tumor or cancer cell. Ideally, the radiolabeled ligand is administered, where the ligand quickly and directly binds to the targeted receptor selectively and to the exclusion of other sites. This is rarely the case. Typically, the radiolabeled ligand is administered and remains in the circulatory system of the subject, with only a small proportion of the ligand binding to the receptor target. The rate at which the ligand binds may be poor, with sufficient binding achieved several hours after administration. Where the ligand remains in the circulatory system, the radioisotope may be delivered to unwanted sites and cause unwanted harm (owing to the emitted radioactivity) or side effects.

Ideally, the ligand itself should show good stability and not undergo decomposition in vivo. This often presents problems, as the functional groups that are present in the ligand may be susceptible to oxidation and subsequent oxidative decomposition. Furthermore, the ligand complexed with the radioisotope should also show good stability. Where the ligand complex decomposes in vivo, the radioisotope is then released and carried throughout the subject, where the radioactivity emitted by the radioisotope leads to damage in unwanted areas.

Where the radiolabeled ligand is administered for the purposes of diagnostic imaging, the ligand should ideally bind to the desired site selectively and any unbound ligand is cleared from the patient. This creates sufficient contrast between the tumor site, for example, where the site to be imaged is a tumor, and the background, where the presence of radioactivity indicates the tumor. Where sufficient contrast is obtained, especially through minimization of background radiation or radiation due to circulating, unbound radioisotope, images of an appropriate quality can then be obtained. Where the radioisotope is released from the ligand, either through decomposition of the ligand or other means, the radioisotope travels through the circulation instead of binding to the tumor (or other) site and contributes to the background radiation in any image taken. This reduces the quality and contrast of the image, which in turn reduces the quality of the information available for diagnostic purposes. While this may be overcome by administering larger amounts of the ligand, in an attempt to encourage greater binding at the desired site, the use of such large amounts of a radioisotope may be detrimental to the subject.

An alternative to the direct binding described above is through the use of an intermediate binding compound. This intermediate binding compound instead binds to the target site and contains a functional group that reacts selectively with a complementary functional group on a ligand that is subsequently administered. There exists a need for ligands that can be radiolabeled and have the capability of binding to an intermediate target site in vivo, where the ligands can be used for the purposes of radiotherapy and diagnostic imaging.

SUMMARY

The present invention is predicated on the discovery that there are compounds that may be used as ligands however do not necessarily target the intended site itself. Instead, the ligands target an intermediate compound that initially binds to the intended site and also has a functional group that can react selectively with the ligand itself. The advantages of this approach are that the reaction between the ligand and the intermediate compound attached to the intended site can be a reaction in which covalent bonds are formed, which allow for more secure attachment of the ligand. The complementary functional groups on the ligand and the intermediate compound can react quickly and selectively with each other. Since the ligand typically contains a radioisotope, the ability of the ligand to react covalently with a specific functional group, rather than a particular receptor (which may be expressed in other, unintended locations), the subsequent localization of the ligand and radioisotope may be improved due to reduced diffusion of the ligand away from the target site.

In one aspect of the present invention, there is provided a compound of Formula (I), or a salt thereof:

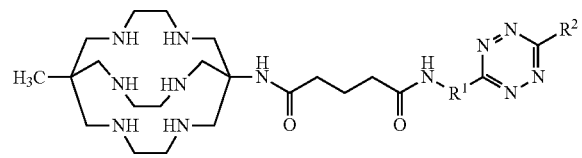

Formula (I)

wherein:
R$^1$ is a linker group; and
R$^2$ is H, optionally substituted alkyl, optionally substituted aryl or optionally substituted heteroaryl.

In an embodiment, the compound of Formula (I) is complexed with a radioisotope.

In another aspect of the present invention, there is provided a composition comprising a compound of Formula (I) or a salt there of according to an earlier aspect.

In another aspect of the present invention, there is provided a kit comprising a compound of Formula (I):

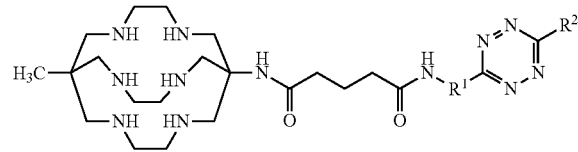

Formula (I)

or a pharmaceutically acceptable salt thereof, the kit comprising:
  a container of a compound of Formula (I), or a pharmaceutically acceptable salt thereof;
  a container comprising a solution of a Cu radioisotope; and
  instructions for preparing an aqueous formulation of a compound of Formula (I), or a pharmaceutically acceptable salt thereof, complexed with a Cu radioisotope.

In an embodiment, the present invention provides a kit according to an earlier aspect, wherein the kit further comprises a container of an antibody comprising a functional group that reacts with the tetrazine moiety of the compound of Formula (I).

In yet another aspect of the present invention, there is provided a method of radioimaging a tumour or cancer in a subject, the method comprising the steps of:
  i) administering to the subject a compound that can bind to a tumour or cancer site and comprises a functional group that reacts with a tetrazine moiety;
  ii) allowing the compound administered in step i) that is not bound to a tumour or cancer site to clear from the subject; and
  iii) administering to the subject a compound of Formula (I), where the compound is complexed with a radioisotope selected from the group consisting of $^{60}$Cu, $^{61}$Cu, $^{64}$Cu and $^{67}$Cu.

In another aspect of the present invention, there is provided a method of treating a tumour or cancer in a subject, the method comprising the steps of:
  i) administering to the subject a compound that can bind to a tumour or cancer site and comprises a functional group that reacts with a tetrazine moiety;
  ii) allowing the compound administered in step i) that is not bound to a tumour or cancer site to clear from the subject; and
  iii) administering to the subject a compound of Formula (I), where the compound is complexed with a radioisotope selected from the group consisting of $^{60}$Cu, $^{61}$Cu, $^{64}$Cu and $^{67}$Cu.

In another aspect of the present invention, there is provided a use of a compound as defined in an earlier aspect or a composition as defined in an earlier aspect in the manufacture of a medicament for treating a cancer or for radioimaging a subject.

In a further aspect of the present invention, there is provided a combination comprising a compound of Formula (I):

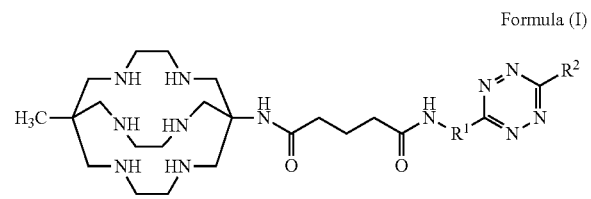

Formula (I)

or a pharmaceutically acceptable salt thereof,
  and a compound that can bind to a tumour or cancer site and that comprises a functional group that reacts with the tetrazine moiety of the compound of Formula (I).

DETAILED DESCRIPTION

The present inventors have found that compounds of Formula (I) may be used as a ligand for radiolabeled compounds.

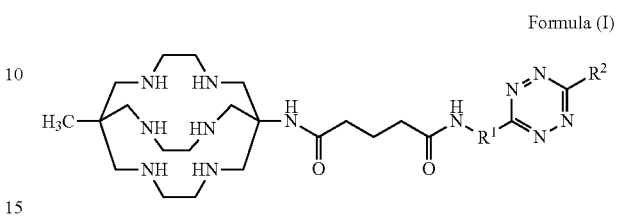

Formula (I)

The compounds of Formula (I) may be labeled with a radioisotope and then used as part of a pre-targeting approach for the treatment and/or imaging of a cancer. The pre-targeting approach requires the prior addition of an intermediate compound to the subject, where the intermediate compound binds to the target site and also contains a moiety to which the compound of Formula (I) selectively and securely binds. This eliminates the need for the direct binding of the radiolabeled compound to the target site and also eliminates the any detrimental side effects owing to the introduction of a radioisotope through a ligand that shows limited binding to the target site.

The intermediate compound that is first introduced to the subject must bind the target site selectively. Examples of such intermediate compounds include antibodies that target the antigens expressed on the surface of the target site. The compound is administered the subject and the compound is allowed to circulate in vivo for a time to allow the compound to bind to the target site. Since the radioisotope is not administered at this point, even if the binding of the intermediate compound to the target site is slow, the unwanted side effects arising from the radioisotope are not observed. The intermediate compound is allowed to eliminate from the subject, which leaves the target site within the subject labelled with a moiety to which the compound of Formula (I) can bind.

The compound of Formula (I) contains a tetrazine moiety, which can participate in a "click-type" reaction, i.e. a cycloaddition reaction, with a coupling partner that has the appropriate functional group. In this situation, the coupling partner with the functional group is on the surface of the target site and is installed through the administration of the intermediate compound described above. The cycloaddition reaction produces "click" adducts that are stable and result in excellent binding of the compound of Formula (I) to the target site, through the intermediate compound.

The tetrazine on the compound of Formula (I) can participate in a click-type reaction with a transcyclooctene moiety. The cycloaddition reaction that occurs between the tetrazine and the transcyclooctene is an inverse electron demand Diels-Alder (IEDDA) reaction, where the tetrazine acts as the diene and the double bond of the transcyclooctene acts as the dienophile. The cycloaddition between a tetrazine and a transcyclooctene is known to be rapid, with a rate constant $k > 30{,}000$ $M^{-1}s^{-1}$. The compound of Formula (I) labeled with a radioisotope is administered to the subject after the intermediate compound comprising a transcyclooctene moiety is allowed to clear. Given the rapidity of the cycloaddition between the tetrazine and transcyclooctene, the administered compound of Formula (I) binds to the transcyclooctene installed on the surface of the target site. This results in the delivery of the radioisotope to the target site.

The compound of Formula (I) comprises a methyl-capped macrocyclic ligand. The macrocyclic ligand is more commonly known as a sarcophagine, or 3,6,10,13,16,19-hexaazabicyclo[6.6.6]icosane, and complexes various transition metal ions. The present inventors have found that the compound of Formula (I) comprising a sarcophagine and a tetrazine can be used successfully in the pretargeting strategy described above for the radiotherapy and diagnostic imaging of tumours. Furthermore, the present inventors have found that the nature of the group linking the tetrazine moiety to the remainder of the molecule (denoted as $R^1$) and the substituting group at the terminal position of the tetrazine (denoted as $R^2$) may be modified.

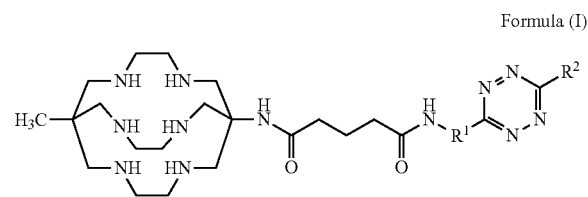

Formula (I)

The linker group $R^1$ ensures that the distance between the target and radioisotope complexed in the sarcophagine is optimised for the target site. Ideally, the linking group $R^1$ is of a length such that the radioisotope contained in the ligand of Formula (I) is of an appropriate distance from the target site. The appropriate distance may vary depending on the nature of the target site, the nature of the intermediate compound that can react with the compound of Formula (I) and the nature of the radioisotope. Additionally, the nature of the linking group should be such that it does not participate in any side reactions, either with other functional groups in the compound or in vivo. In some embodiments, $R^1$ is an optionally substituted alkylene linker group. In some embodiments, $R^1$ is an optionally substituted arylene linker group. In an embodiment, $R^1$ is a benzylene (—$CH_2C_6H_4$—) group.

Accordingly, the compounds of Formula (I) may have the structure of Formula (I'), where $R^1$ is a benzylene group:

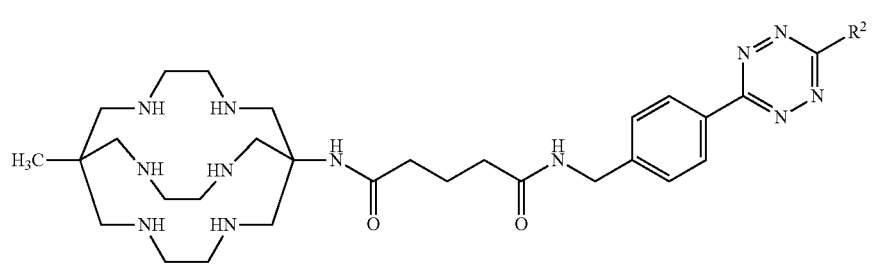

Formula (I')

where $R^2$ is as defined above.

The substituent $R^2$ is at the terminal position of the tetrazine. The steric and/or electronic nature of the substituent $R^2$ may affect the rate of the click-type reaction between the tetrazine and coupling partner, for example, a transcyclooctene moiety. In an embodiment, $R^2$ is H. In another embodiment, $R^2$ is an optionally substituted alkyl group. In another embodiment, $R^2$ is an optionally substituted aryl group. In an embodiment, $R^2$ is an optionally substituted heteroaryl group.

The term "optionally substituted" as used throughout the specification denotes that the group may or may not be further substituted or fused (so as to form a condensed polycyclic system), with one or more non-hydrogen substituent groups. In certain embodiments the substituent groups are one or more groups independently selected from the group consisting of halogen, =O, =S, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —C(=O)OH, —C(=O)Ra, —C(=O)ORa, —C(=O)$NR^aR^b$, —C(=NOH)$R^a$, —C(=$NR^a$)$NR^bR^c$, —$NR^aR^b$, —$NR^aC$(=O)$R^b$, —$NR^aC$(=O)$OR^b$, —$NR^aC$(=O)$NR^bR^c$, —$NR^aC$(=$NR^b$)$NR^cR^d$, —$NR^aSO_2R^b$, —$SR^a$, —$SO_2NR^aR^b$, —$OR^a$, —OC(=O)$NR^aR^b$, —OC(=O)$R^a$ and acyl, wherein $R^a$, $R^b$, $R^c$ and $R^d$ are each independently selected from the group consisting of H, $C_1$-$C_{12}$alkyl, $C_1$-$C_{12}$haloalkyl, $C_2$-$C_{12}$alkenyl, $C_2$-$C_{12}$alkynyl, $C_2$-$C_{10}$ heteroalkyl, $C_3$-$C_{12}$cycloalkyl, $C_3$-$C_{12}$cycloalkenyl, $C_2$-$C_{12}$heterocycloalkyl, $C_2$-$C_{12}$ heterocycloalkenyl, $C_6$-$C_{18}$aryl, $C_1$-$C_{18}$heteroaryl, and acyl, or any two or more of $R^a$, $R^b$, $R^c$ and $R^d$, when taken together with the atoms to which they are attached form a heterocyclic ring system with 3 to 12 ring atoms.

In some embodiments, each optional substituent is independently selected from the group consisting of: halogen, =O, =S, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkyloxy, alkyloxyalkyl, alkyloxyaryl, alkyloxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, —COOH, —SH, and acyl.

Examples of particularly suitable optional substituents include F, Cl, Br, I, $CH_3$, $CH_2CH_3$, OH, $OCH_3$, $CF_3$, $OCF_3$, $NO_2$, $NH_2$, and CN.

"Alkyl" as a group or part of a group refers to a straight or branched aliphatic hydrocarbon group, preferably a $C_1$-$C_{12}$alkyl, more preferably a $C_1$-$C_{10}$ alkyl, most preferably $C_1$-$C_6$ unless otherwise noted. Examples of suitable straight and branched $C_1$-$C_6$ alkyl substituents include methyl, ethyl, n-propyl, 2-propyl, n-butyl, sec-butyl, t-butyl, hexyl, and the like. The group may be a terminal group or a bridging group.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_5$-$C_7$ cycloalkyl or $C_5$-$C_7$ cycloalkenyl group are fused together to form a cyclic structure, such as tetrahydronaphthyl, indenyl or indanyl. The group may be a terminal group or a bridging group. Typically an aryl group is a $C_6$-$C_{18}$ aryl group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl, 1-, 2-, or 3-indolyl, and 2-, or 3-thienyl. A heteroaryl group is typically a $C_1$-$C_6$ heteroaryl group. The group may be a terminal group or a bridging group.

Examples of compounds of Formula (I) include:

| Compound No. | Structure |
| --- | --- |
| 1 | 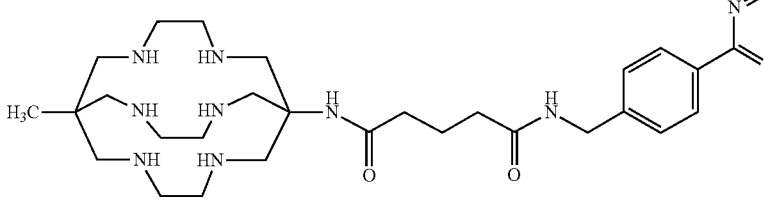 |
| 2 | 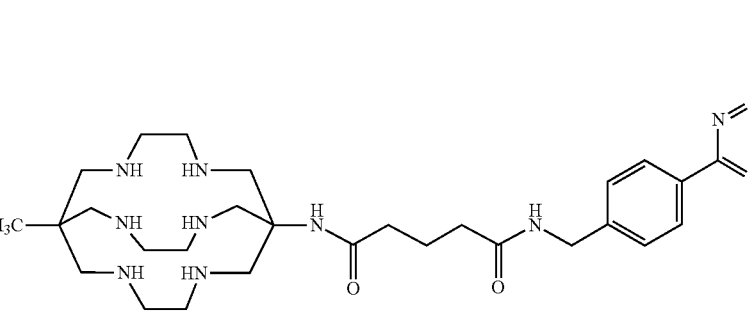 |
| 3 | 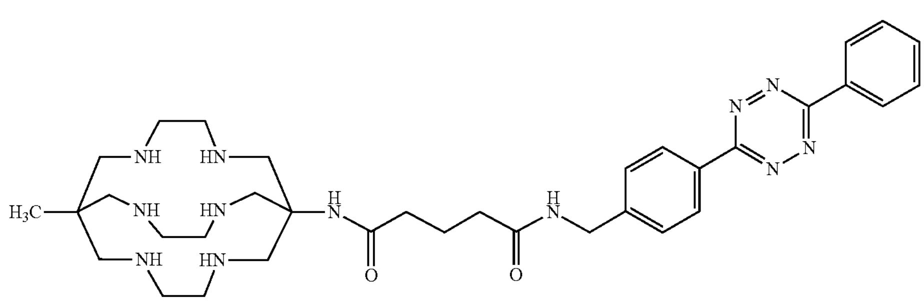 [SMILES: CC12CNCCNCC(NC(=O)CCCC(=O)NCc3ccc(-c4nnc(-c5ccccc5)nn4)cc3)(CNCCNC1)CNCCNC2] |

-continued

| Compound No. | Structure |
|---|---|
| 4 | 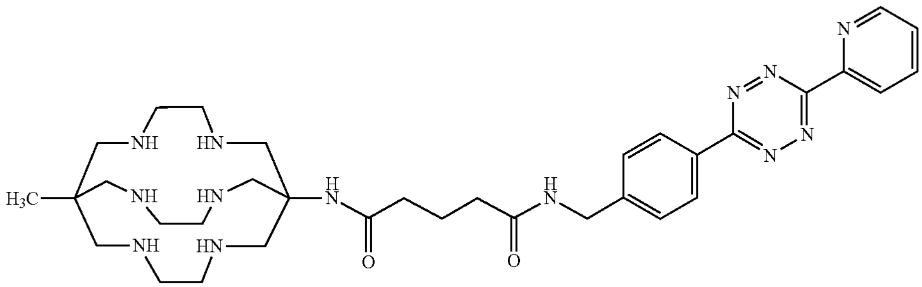 [SMILES: CC12CNCCNCC(NC(=O)CCCC(=O)NCc3ccc(-c4nnc(-c5ccccn5)nn4)cc3)(CNCCNC1)CNCCNC2] |
| 5 | 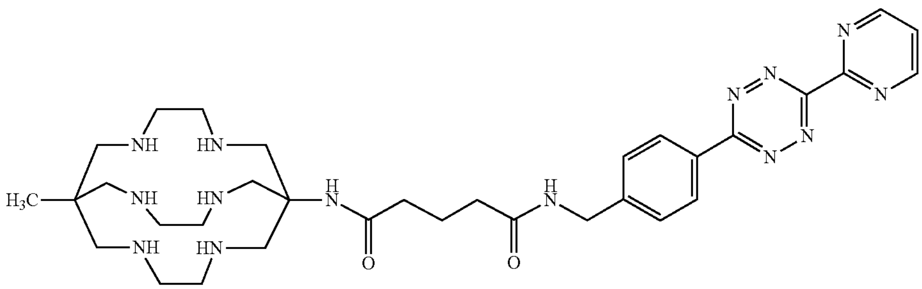 [SMILES: CC12CNCCNCC(NC(=O)CCCC(=O)NCc3ccc(-c4nnc(-c5ncccn5)nn4)cc3)(CNCCNC1)CNCCNC2] |
| 6 | 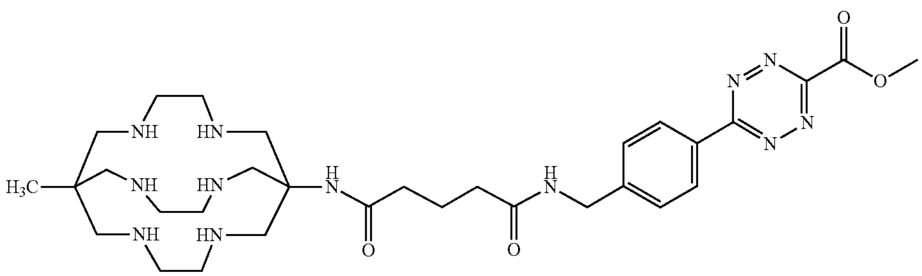 |
| 7 | 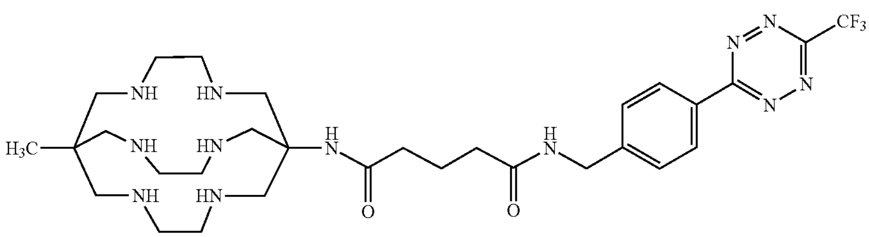 [SMILES: CC12CNCCNCC(NC(=O)CCCC(=O)NCc3ccc(-c4nnc(C(F)(F)F)nn4)cc3)(CNCCNC1)CNCCNC2] |
| 8 | 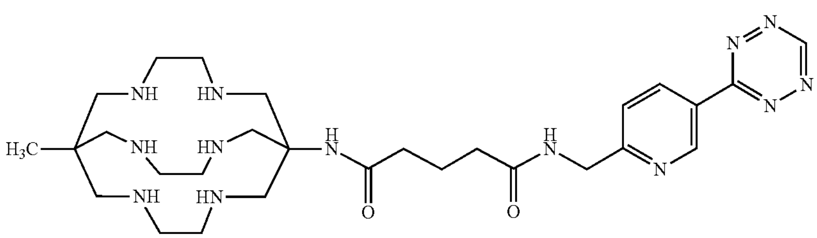 |
| 9 | 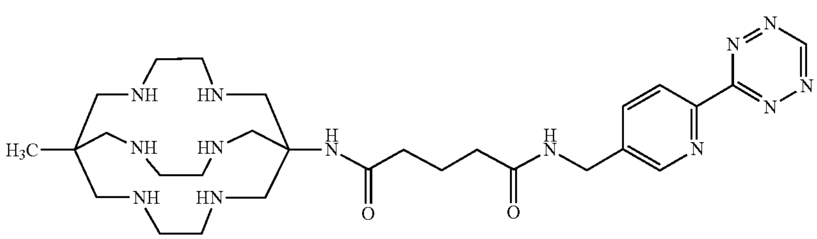 [SMILES: CC12CNCCNCC(NC(=O)CCCC(=O)NCc3ccc(-c4nncnn4)nc3)(CNCCNC1)CNCCNC2] |

The compounds of the present invention may be complexed with a radioisotope. In some embodiments, the radioisotope is an isotope of copper. In some embodiments, the radioisotope is a radionuclide selected from the group consisting of $^{60}$Cu, $^{61}$Cu, $^{64}$Cu and $^{67}$Cu.

Without wishing to be bound by theory, it has been found that the compounds described herein provide one or more advantages over similar compounds known in the art. The compounds of the present invention comprising a sarcophagine cage bearing a terminal methyl substituent and a single propyl linker adjacent to the sarcophagine, show better retention of the radioisotope complexed by the ligand, such that the ligand-radioisotope complex shows greater stability overall. It is believed that the combination of the methyl group and absence of the aminobenzylene linker from the compound provides the advantages now observed. One advantage of increased retention of the radioisotope includes the reduction in side effects and unwanted damage to other parts of the subject, due to any free radioisotope released from the ligand. Another advantage is that the radioisotope is more efficiently used and delivered to the intended site of action, where the radioisotope is not released unnecessarily. Yet another advantage is that the time for which the ligand-radioisotope is useful, once administered, is greater than that for similar compounds.

The compounds and complexes of the present invention may be administered in a manner that makes the compound available for the desired application, for example, for radiotherapy or diagnostic imaging. One skilled in the art of preparing compositions or formulations of this type would be aware of the proper form and mode of administration, where the form and mode of administration depend on the compound, the condition to be treated and other circumstances.

The compounds and complexes of the present invention may be administered either alone or in the form of a pharmaceutical composition in combination with a pharmaceutically acceptable carrier, diluent or excipient. The compounds and complexes of the present invention, while effective alone, may be formulated and administered in the form of a pharmaceutically acceptable salt, as the salt form of the compound may show better stability, solubility or crystallinity. The compounds and complexes of the present invention are typically used in the form of compositions comprising the compound or complex, the formulation of which depends on the mode of administration and the purpose or condition to be treated. Another advantage of the compounds of the present invention is that they are remarkably stable in formulations or compositions, when compared to similar compounds. In this regard, formulations of the compounds of the present invention complexed with a radioisotope undergo less radiolysis when compared to similar compounds. Radiolysis leads to the breaking of bonds in the ligand due to the energy released during spontaneous radioactive decay of the radioisotope. This then leads to the release of the free radioisotope, which may then circulate and damage nearby tissues. In addition to unwanted tissue damage, radiolysis leads to a reduction in the overall efficacy of the radioisotope-ligand complex. The present inventors have found that a radiolabeled complex of compounds of the present invention may have the requisite stability in a pharmaceutical formulation, without the need for the addition of one or more stabilisers to the formulation. Without wishing to be bound by theory, the present inventors believe that the overall structure of the compounds of the present invention provide the stability observed in the corresponding radiolabeled complexes when formulated.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

Although the compounds and complexes of the present invention may show some stability in a pharmaceutical formulation or composition in the absence of any stabilisers, the formulations may still comprise one or more excipients. These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

According to another aspect of the present invention, there is provided a kit comprising a compound of Formula (I):

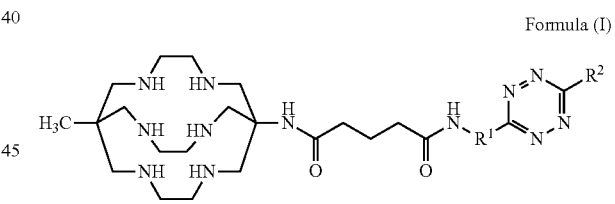

Formula (I)

or a pharmaceutically acceptable salt thereof, the kit comprising:
a container of a compound of Formula (I), or a pharmaceutically acceptable salt thereof;
a container comprising a solution of a Cu radioisotope; and
instructions for preparing an aqueous formulation of a compound of Formula (I), or a pharmaceutically acceptable salt thereof, complexed with a Cu radioisotope.

The kits of the present invention may further comprise a container consisting of excipients and/or stabilizers and instructions for the addition of said excipients and/or stabilisers.

Uses of the Compounds of the Present Invention

The compounds of the present invention may be particularly useful for the purpose of diagnosis and treatment in medicine. Complexes with a ligand bearing an appropriate targeting fragment and radioisotope can be used to locate and treat specific tissue types. For such complexes to be considered suitable for use in in vivo diagnosis and treatment, the complex must display the appropriate kinetic, stability and clearance properties under physiological conditions, in addition to the requisite solubility and stability properties of the complex in solution. As used herein, the term "complex" may relate to a ligand-metal ion complex, where the metal ion is a radioactive isotope, or alternatively, the metal ion is a non-radioactive isotope. As described earlier, the use of the compounds of the present invention for the purpose of diagnosis and treatment relies on the introduction of an intermediate compound that binds the target site and also binds the compound of Formula (I).

Accordingly, the present invention provides a method for radioimaging, a method for diagnosing a disease in a subject or a method for therapy of a disease in a subject, comprising administering to the subject an effective amount of a compound as defined herein. The present inventors have found that the compounds of the present invention may be used in a method for radioimaging, a method for diagnosing or a method for therapy of a cancer.

As used herein the term "cancer" broadly encompasses a class of neoplastic diseases characterised with abnormal cell growth with the potential to invade or spread to other parts of the body. These are to be contrasted with benign tumours, which do not spread to other parts of the body and therefore the definition as used herein includes all malignant (cancerous) disease states. The term therefore encompasses the treatment of tumours.

Accordingly, the term "tumour" is used generally to define any malignant cancerous or pre-cancerous cell growth, and may include leukemias, but is particularly directed to solid tumours or carcinomas such as melanomas, colon, lung, ovarian, skin, breast, pancreas, pharynx, brain, prostate, CNS, and renal cancers (as well as other cancers).

The radioisotope-ligand complex of the present invention may comprise a radioisotope such as $^{64}Cu$. The $^{64}Cu$ isotope has a half-life of approximately 12.7 hours and decays by both positron emission and beta decay, which makes the use of a $^{64}Cu$-labelled complex suitable for use in various modes of radioimaging. In particular, the decay characteristics and half-life of $^{64}Cu$ make this radioisotope a favourable choice for use in positron emission tomography (PET) and single-photon emission computed tomography (SPECT). The radioisotope-ligand complex of the present invention may comprise a radioisotope such as $^{61}Cu$. The $^{61}Cu$ isotope has a half-life of approximately 3 hours and decays by positron emission, which makes the use of a $^{61}Cu$-labelled complex suitable for use in various modes of radioimaging. The radioisotope-ligand complex of the present invention may also comprise a radioisotope such as $^{67}Cu$. The $^{67}Cu$ isotope has a half-life of approximately 61.8 hours and decays by beta emission, which makes the use of a $^{67}Cu$-labelled complex suitable for use in SPECT imaging. The $^{67}Cu$-labelled complex may also be suitable for use as a radiotherapy treatment.

In an embodiment, the present invention provides a method of radioimaging a tumour or cancer in a subject, the method comprising the steps of:
i) administering to the subject a compound that can bind to a tumour or cancer site and comprises a functional group that reacts with a tetrazine moiety;
ii) allowing the compound administered in step i) to clear from the subject; and
iii) administering to the subject a compound of Formula (I), where the compound is complexed with a radioisotope selected from the group consisting of $^{60}Cu$, $^{61}Cu$, $^{64}Cu$ and $^{67}Cu$.

The administration of an effective amount of a compound of Formula (I) and a Cu radioisotope, such as $^{60}Cu$, $^{61}Cu$, $^{64}Cu$ or $^{67}Cu$ may lead to the binding of the ligand and radioisotope to the intermediate compound, where the intermediate compound is bound to the target site. The target site may be the surface of a tumour. In an embodiment, the present invention provides a method for radioimaging, comprising administering to the subject a compound of Formula (I) and a Cu ion. In an embodiment, a formulation comprising a compound of Formula (I) and a $^{64}Cu$ or $^{67}Cu$ ion may be used in a method for radioimaging. Monitoring of a subject to which a compound of Formula (I) and a Cu radioisotope was administered, after administration of an intermediate compound, by PET or SPECT, for example, allows for the visualization and subsequent detection of tumour sites. The visualization information obtained by radioimaging may provide information in relation to the location of any such tumour sites. This provides information in relation to the location of the tumours, where present. Repeated imaging at later timepoints allows for monitoring clearance of the radioisotope-ligand complex, which enables dosimetry estimates to be calculated. A person skilled in the art would understand that the amount to be administered in order to facilitate radioimaging may vary and will subsequently depend on the nature of the subject and the intended site of imaging.

The compounds of the present invention may be administered to a subject for the purposes of radioimaging, diagnosis or therapy. Administration is by a parenteral route, with administration by intravenous injection preferred. Alternatively, the formulations of the present invention may be given by intraarterial or other routes, for delivery into the systemic circulation. The subject to which the compound is administered is then placed into a PET scanner and images showing the localisation of the radioisotope-ligand complex, and subsequently location of any tumours, are obtained. This then allows for diagnosis and detection of tumours.

In an embodiment, the present invention provides the use of a compound of Formula (I) in a method for the radioimaging of a tumour or cancer. One skilled in the art would understand that the information obtained from radioimaging of a subject may be used in the diagnosis of a tumour or cancer in the subject. In an embodiment, the present invention provides a method for the diagnosis of a tumour or cancer. In an embodiment, the present invention provides a method for the diagnosis of a colorectal carcinoma.

In an embodiment, the present invention provides a method of treating a tumour or cancer in a subject, the method comprising the steps of:
i) administering to the subject a compound that can bind to a tumour or cancer site and comprises a functional group that reacts with a tetrazine moiety;
ii) allowing the compound administered in step i) to clear from the subject; and
iii) administering to the subject a compound of Formula (I), where the compound is complexed with a radioisotope selected from the group consisting of $^{60}Cu$, $^{61}Cu$, $^{64}Cu$ and $^{67}Cu$.

As described above, the compound of Formula (I) binds to an intermediate compound that is already bound to the target site. An example of an intermediate compound is a compound that contains a transcyclooctene group, since such a functional group can react with the tetrazine of the compound Formula (I) in a cyclisation reaction which securely binds the compound of Formula (I) to the intermediate compound. The intermediate compound also contains a functionality that binds to a specific tumour or cancer site by recognition of a particular receptor or the like that is characteristic of a tumour or cancer. In this regard, the intermediate compound may be an antibody that binds to an antibody that is expressed on the surface of the tumour or cancer site. Where the intermediate compound is an antibody, it may be modified so as to contain a functional group that reacts with the tetrazine, such as a transcyclooctene functional group. For the purposes of diagnosis or therapy, the intermediate compound is first administered to the subject and allowed to bind to the targeted tumour or cancer site. Where there is a fraction of the intermediate compound administered remains unbound to a cancer or tumour site, the remainder of this unbound intermediate compound is then allowed to clear from the circulation of the subject. The compound of Formula (I) is then administered to the subject and selectively targets the intermediate compound bearing the functional group that reacts with the tetrazine moiety in the compound of Formula (I). In allowing the unbound portion of the intermediate compound to clear from the circulation of the subject, the subsequent administration of the compound of Formula (I) is eventually attached and localized only where the intermediate compound is located and not in the general circulation. This improves the specificity of the radioisotope that is delivered with the compound of Formula (I). Where the intermediate compound contains a transcyclooctene moiety, a click type reaction between the transcyclooctene and the tetrazine in the compound of Formula (I) occurs, which securely binds the compound of Formula (I) to the intermediate compound. Where the compound of Formula (I) contains a radioisotope, this is then localized at the targeted tumour or cancer site. The products resulting from the spontaneous decay of the radioisotope are detected and an image showing the location of the radioisotope may be generated. Alternatively, or concurrently, the radioactive decay products may be useful in treating the tumour or cancer that has resulted in the initial expression of the antigen.

Where the intermediate compound is an antibody, it may be modified so as to contain a functional group that reacts with the tetrazine of the compound of Formula (I). An example of an antibody that may be modified so as to include such a functional group (e.g. a transcyclooctene group) is huA33, a monoclonal antibody that recognizes the A33 antigen. The A33 antigen is typically expressed in cancers such as colorectal cancer. Where the intermediate compound is a modified transcyclooctene-huA33 antibody, the compound of Formula (I) may be used in the detection and diagnosis of colorectal cancer by radioimaging. Additionally, the compound of Formula (I) may also be used in the treatment of colorectal cancer.

In an embodiment, the compound comprising a functional group that reacts with a tetrazine moiety is an antibody.

Accordingly, in an embodiment, the present invention provides a method of radioimaging a tumour or cancer in a subject, the method comprising the steps of:
i) administering to the subject an antibody comprising a transcyclooctene group;
ii) allowing the antibody administered in step i) to clear from the subject; and
iii) administering to the subject a compound of Formula (I), where the compound is complexed with a radioisotope selected from the group consisting of $^{60}$Cu, $^{61}$Cu, $^{64}$Cu and $^{67}$Cu.

In another embodiment, the present invention provides a method of treating a tumour or cancer in a subject, the method comprising the steps of:
i) administering to the subject an antibody comprising a transcyclooctene group;
ii) allowing the antibody administered in step i) to clear from the subject; and
iii) administering to the subject a compound of Formula (I), where the compound is complexed with a radioisotope selected from the group consisting of $^{60}$Cu, $^{61}$Cu, $^{64}$Cu and $^{67}$Cu;
wherein the cancer is colorectal cancer.

Where the compound of Formula (I) is complexed with a Cu radioisotope, the administration of the complex of Formula (I) and a Cu ion may treat a tumour or cancer. As discussed above, the compound of Formula (I) binds to an intermediate compound administered prior to the compound of Formula (I), where the intermediate compound comprising a transcyclooctene group, for example, is first bound to the tumour or the cancer. Binding of the compound of Formula (I) and the Cu radioisotope brings the radioisotope into close proximity to the target site. As the Cu radioisotope undergoes radioactive decay, the products of decay may be useful in the treatment of the tumour or cancer.

In an embodiment, the radioimaging is positron emission tomography (PET). In an embodiment, the radioisotope is $^{64}$Cu. In another embodiment, the radioisotope is $^{67}$Cu. Where the compound of Formula (I) is complexed with a radioisotope and is used in a method for radioimaging a subject, the intermediate compound comprising a transcyclooctene group, for example, is first bound to the site to be imaged. Binding of the compound of Formula (I) and the Cu radioisotope brings the radioisotope into close proximity to the imaging site. As the Cu radioisotope undergoes radioactive decay, the products of decay are detected and allow for an image to be developed.

According to another embodiment of the present invention, there is provided a combination of a compound of Formula (I):

Formula (I)

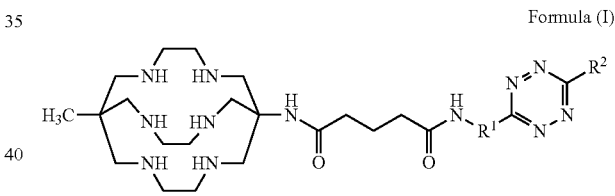

or a pharmaceutically acceptable salt thereof,
and a compound containing a functional group that reacts with the tetrazine moiety of the compound of Formula (I).

The combination of a compound of Formula (I) and compound containing a functional group that reacts with the tetrazine moiety of the compound of Formula (I) may be provided such that they compounds are administered sequentially so as to allow for the compound containing the functional group that reacts with the tetrazine to bind to the selected site.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

EXAMPLES

1. Synthesis of Compounds of Formula (I)

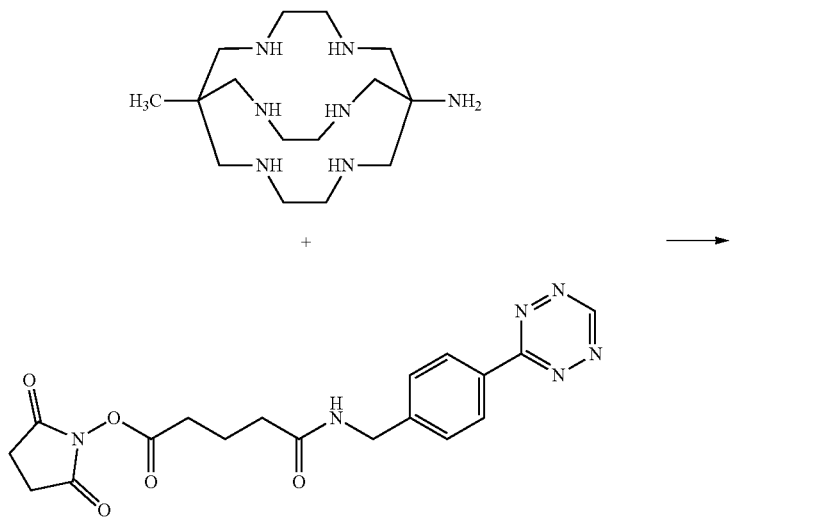

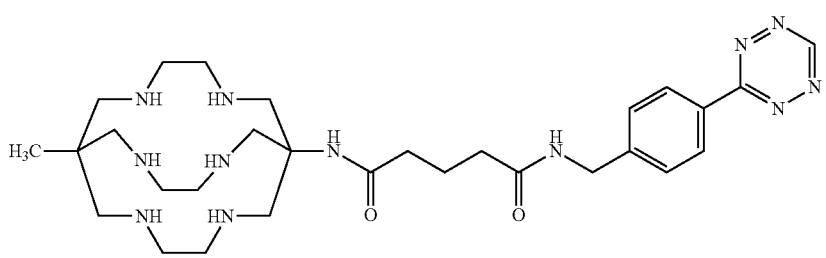

The above compound of Formula (I) may be synthesized by coupling an amino-substituted sarcophagine with a phthalimide ester derivative of the propyl linker/tetrazine functionality. The coupling reaction may require a coupling agent, for example, a peptide coupling agent. The coupling reaction may also require one or more bases to proceed.

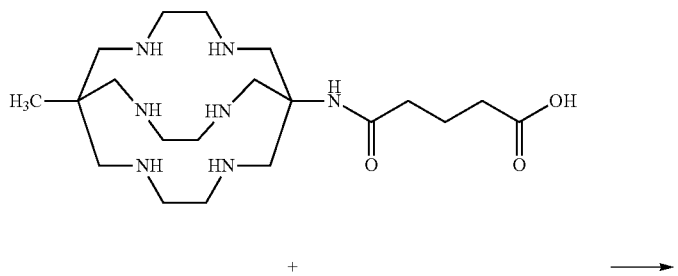

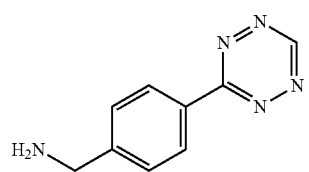

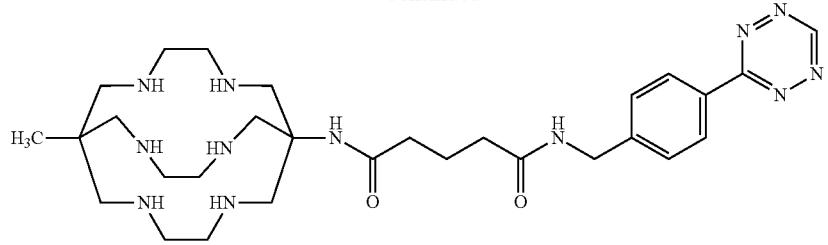

Alternatively, the above compound of Formula (I) may be synthesised under standard peptide conditions between the carboxylic acid derivative of the linker-bound sarcophagine and the corresponding amine.

2. Synthesis of Complexes of Formula (I)

A copper(II) ion complex of Formula (I) may be prepared by adding a solution of a copper(II) salt to a solution of a compound of Formula (I).

The invention claimed is:

1. A compound of Formula (I), or a salt thereof:

Formula (I)

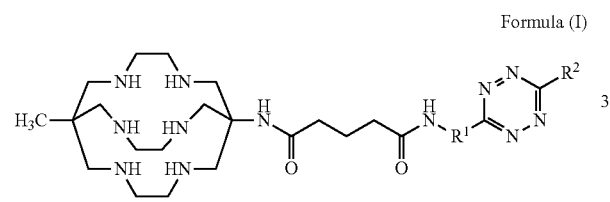

wherein:
R$^1$ is a linker group; and
R$^2$ is optionally substituted alkyl, optionally substituted aryl or optionally substituted heteroaryl.

2. A compound according to claim 1, wherein R$^1$ comprises an arylene group.

3. A compound according to claim 2, wherein R$^1$ is a benzylene group.

4. A compound according to claim 1, wherein the compound is coordinated with a Cu ion.

5. A compound according to claim 4, wherein the Cu ion is selected from the group consisting of $^{60}$Cu, $^{61}$Cu, $^{64}$Cu and $^{67}$Cu.

6. A composition comprising a compound according to claim 1.

7. A kit comprising a compound of Formula (I):

Formula (I)

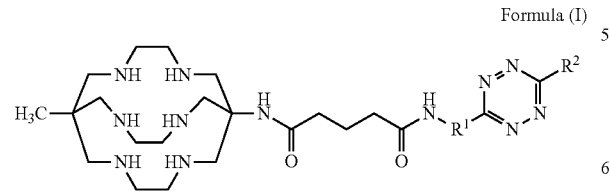

or a pharmaceutically acceptable salt thereof,
wherein:
R$^1$ is a linker group; and
R$^2$ is optionally substituted alkyl, optionally substituted aryl or optionally substituted heteroaryl;

the kit comprising:
a container of a compound of Formula (I), or a pharmaceutically acceptable salt thereof;
a container comprising a solution of a Cu radioisotope; and
instructions for preparing an aqueous formulation of a compound of Formula (I), or a pharmaceutically acceptable salt thereof, complexed with a Cu radioisotope.

8. A method of treating a tumour or a cancer in a subject, the method comprising the steps of:
i) administering to the subject a compound that can bind to a tumour or cancer site and comprises a functional group that reacts with a tetrazine moiety;
ii) allowing the unbound fraction of the compound administered in step i) to clear from the subject; and
iii) administering to the subject a compound of Formula (I) according to claim 1, where the compound is complexed with a radioisotope selected from the group consisting of $^{60}$Cu, $^{61}$Cu, $^{64}$Cu and $^{67}$Cu, wherein the functional group of the compound that can bind to a tumour or cancer site that reacts with a tetrazine moiety further comprises a transcyclooctene group.

9. A method of radioimaging a tumour or cancer in a subject, the method comprising the steps of:
i) administering to the subject a compound that can bind to a tumour or cancer site and comprises a functional group that reacts with a tetrazine moiety;
ii) allowing the unbound fraction of the compound administered in step i) to clear from the subject;
iii) administering to the subject a compound of Formula (I) according to claim 1, where the compound is complexed with a radioisotope selected from the group consisting of $^{60}$Cu, $^{61}$Cu, $^{64}$Cu and $^{67}$Cu; and
iv) radioimaging the tumour or cancer site, wherein the functional group of the compound that can bind to a tumour or cancer site that reacts with a tetrazine moiety further comprises a transcyclooctene group.

10. A method according to claim 8, wherein the compound comprising a transcyclooctene group is an antibody.

11. A method according to claim 8, wherein the cancer is colorectal cancer.

12. A combination comprising a compound of Formula (I):

Formula (I)

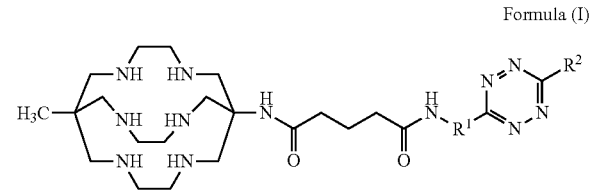

or a pharmaceutically acceptable salt thereof,
wherein:
R¹ is a linker group; and
R² is optionally substituted alkyl, optionally substituted aryl or optionally substituted heteroaryl;
and a compound that can bind to a tumour or cancer site and that comprises a functional group that reacts with the tetrazine moiety of the compound of Formula (I), wherein the functional group of the compound that can bind to a tumour or cancer site that reacts with a tetrazine moiety further comprises a transcyclooctene group.

13. A method according to claim 9, wherein the compound comprising a transcyclooctene group is an antibody.

14. A method according to claim 9, wherein the cancer is colorectal cancer.

15. A compound according to claim 1 selected from the group consisting of:

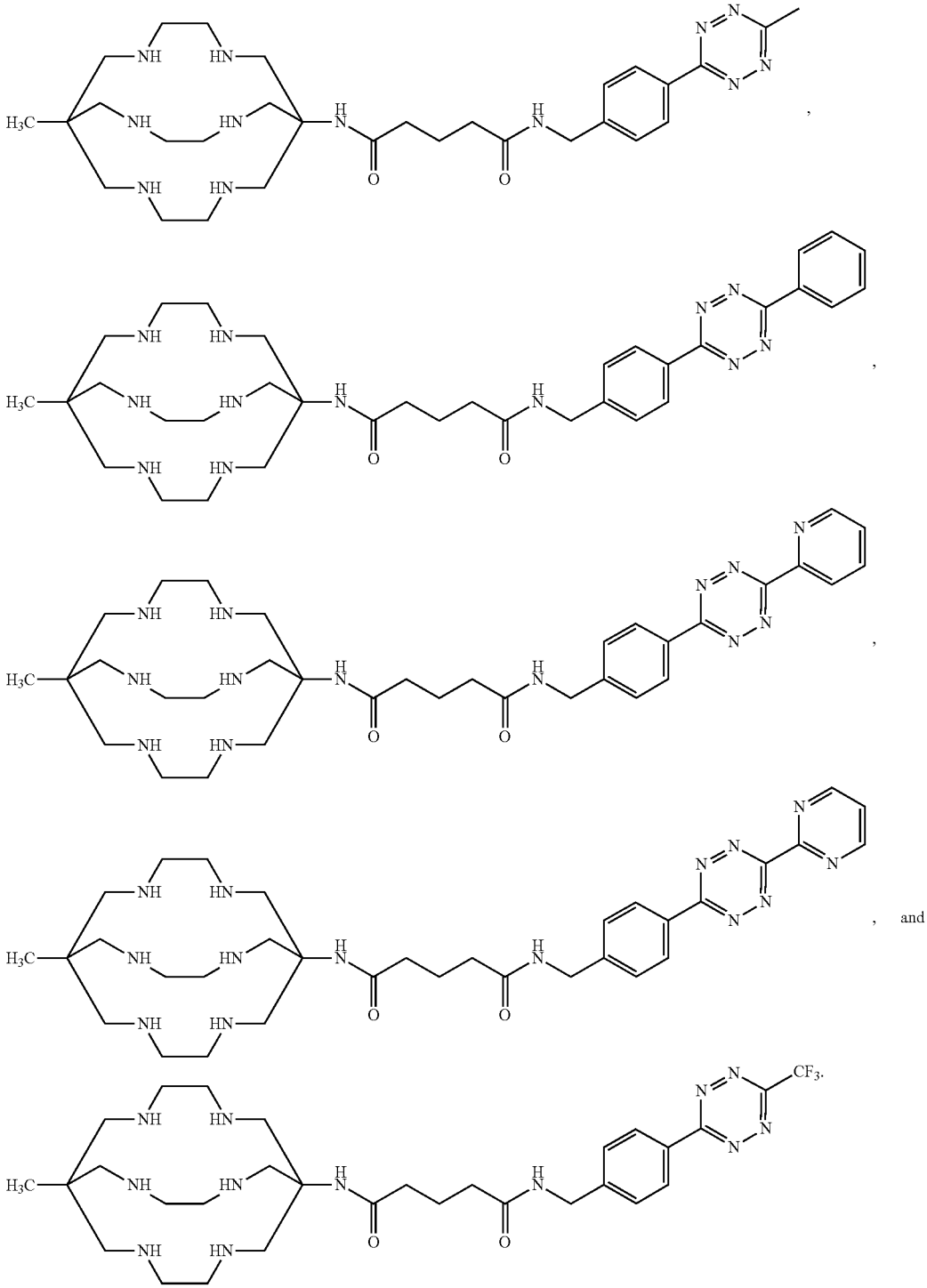

16. A compound comprising
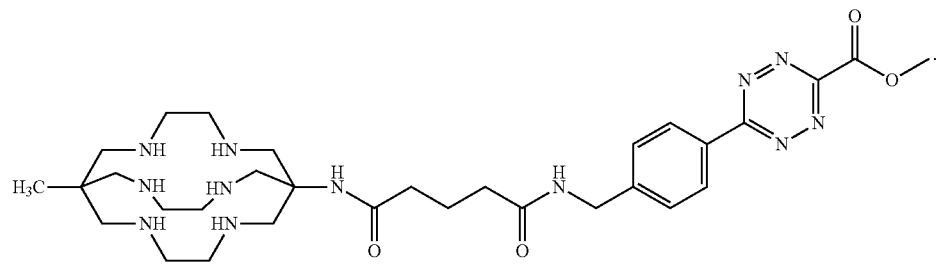
* * * * *